United States Patent
Ikemoto et al.

(10) Patent No.: US 7,119,215 B2
(45) Date of Patent: Oct. 10, 2006

(54) PRODUCTION METHOD OF CITALOPRAM, INTERMEDIATE THEREFOR AND PRODUCTION METHOD OF THE INTERMEDIATE

(75) Inventors: Tetsuya Ikemoto, Osaka (JP); Wei-Guo Gao, Osaka (JP); Masami Igi, Osaka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 1806 days.

(21) Appl. No.: 10/086,076

(22) Filed: Feb. 28, 2002

(65) Prior Publication Data
US 2002/0095051 A1    Jul. 18, 2002

Related U.S. Application Data

(62) Division of application No. 09/654,768, filed on Sep. 5, 2000, now Pat. No. 6,433,196.

(30) Foreign Application Priority Data

Feb. 17, 2000 (JP) .............. 2000/39936
Mar. 9, 2000 (JP) .............. 2000/65527

(51) Int. Cl.
*C07D 307/78* (2006.01)
(52) U.S. Cl. .................................. 549/469
(58) Field of Classification Search ............. 549/469
See application file for complete search history.

(56) References Cited

U.S. PATENT DOCUMENTS

| | | | |
|---|---|---|---|
| 3,642,997 A | 2/1972 | Shen et al. | |
| 3,835,167 A | 9/1974 | Pfister | |
| 4,136,193 A | 1/1979 | Bøgesø et al. | |
| 5,061,810 A | 10/1991 | Ramachandran | |
| 6,310,222 B1 | 10/2001 | Ikemoto et al. | |
| 2002/0004604 A1 | 1/2002 | Petersen et al. | |
| 2003/0060640 A1 | 3/2003 | Petersen | |
| 2003/0083508 A1 | 5/2003 | Petersen et al. | |
| 2003/0109577 A1 | 6/2003 | Liljegren et al. | |
| 2003/0114692 A1 | 6/2003 | Peterson et al. | |
| 2003/0134895 A1 | 7/2003 | Petersen et al. | |

FOREIGN PATENT DOCUMENTS

| | | |
|---|---|---|
| DE | 26 57 013 A1 | 7/1977 |
| EP | 0 178 184 A1 | 4/1986 |
| WO | WO 93/14055 | 7/1993 |
| WO | WO 98/19511 | 5/1998 |
| WO | WO 99/30548 A2 | 6/1999 |
| WO | WO 01/68632 | 9/2001 |
| WO | WO 01/85712 | 11/2001 |

OTHER PUBLICATIONS

Allinger, "Organic Chemistry,", pp. 452-455 (1971).*
Dokunikhin et al., "Anthraquinone Derivatives. III. Sysnthesis of Fluoro-substituted 2-Anthraquinone-Carbonxylic Acid and 2-Aminoanthraquinone," *Chemical Abstracts*, 60 (13) (XP-002166788) (1964).
Bigler et al., "Quantitative Structure-Activity Relationships in a Series of Selective 5-HT Uptake Inhibitors," *European Journal of Medicinal Chemistry, Editions Scientifique Elsevier*, 12 (3), 289-295 (XP-000944915) (1977).
Goethals et al., "Basicity of Benzophenones and Polysubstituted 2-Methylbenzophenones. Role of Molecular Twisting and Electronic Interactions in the Transmission of Substituent Effects," *Chemical Abstracts Service*, Database Accession No. 83:178083 (XP-002190939) (1975) (abstract).
Verbeerst et al., "Friedel-Crafts Acylation. V. Polar and Steric Substituent Effects in the Reaction of Disubstituted Benzoyl Chlorides Carrying a Constant Ortho-Substituent," *Chemical Abstracts Service*, Database Accession No. 70:2962 (XP-002190940) (1969) (abstract).

* cited by examiner

*Primary Examiner*—Samuel Barts
(74) *Attorney, Agent, or Firm*—Leydig, Voit & Mayer, Ltd.

(57) ABSTRACT

A compound of formula [V] is prepared by oxidizing a compound of formula [III]. Citalopram can be industrially and economically produced and at a high yield by converting a compound of formula [V], which is prepared from a compound of formula [III], to a compound of formula [VI], and then alkylating the compound of formula [VI] to form citalopram.

8 Claims, No Drawings ically advantageous production method capable of industrial and economical production of citalopram at a high yield under basic conditions wherein specific bases are combined.

PRODUCTION METHOD OF CITALOPRAM, INTERMEDIATE THEREFOR AND PRODUCTION METHOD OF THE INTERMEDIATE

CROSS REFERENCE TO RELATED APPLICATIONS

This patent application is a divisional of U.S. patent application Ser. No. 09/654,768, filed Sep. 5, 2000 now U.S. Pat. No. 6,433,196.

TECHNICAL FIELD OF THE INVENTION

The present invention relates to a production method of citalopram useful as an antidepressant, a synthetic intermediate therefor and a production method of the intermediate.

BACKGROUND OF THE INVENTION

Citalopram having the formula [A]

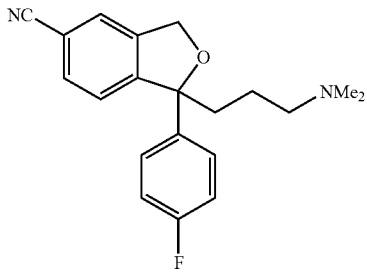

[A]

is useful as an antidepressant. As a production method of citalopram, there is known a method comprising the use of a 5-phthalancarbonitrile compound of the formula [VI]

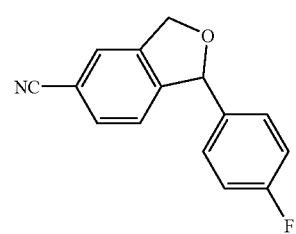

[VI]

hereinafter to be also referred to as compound [VI]. For example, compound [VI] is reacted with 3-(dimethylamino)propyl halide in the presence of a condensing agent (JP-B-61-35986). In this publication, sodium hydride is used as a condensing agent. According to this method, citalopram is obtained at a low yield, and therefore, this method is not necessarily a preferable one. Moreover, this publication does not teach how to increase the yield, not to mention the use of a different additive besides the condensing agent to improve the yield.

As a different production method of citalopram, there is reported reaction of compound [VI] with 3-(dimethylamino)propyl halide under basic conditions (WO98/19511). In this publication, lithium diisopropylamide obtained from n-butyllithium and diisopropylamine is used as a base. While the yield is improved, expensive n-butyllithium is necessary and a reaction at a very low temperature (Example, from −50° C. to −40° C.) is required, which makes the method industrially unpreferable. This publication does not teach an economical base that permits reaction in a typical temperature range, or industrial and economical production of citalopram at a high yield under basic conditions wherein specific bases are combined.

It is therefore an object of the present invention to provide an economical and industrially advantageous production method of citalopram, which affords production of citalopram at high yields.

Another object of the present invention is to provide a novel production method of a compound represented by the formula [III] to be mentioned later.

SUMMARY OF THE INVENTION

For this purpose, the method described in JP-B-61-35986 utilizing a condensing agent has been improved. According to the present invention, a method comprising adding, besides a condensing agent, at least one of N,N,N',N'-tetramethylethylenediamine and 1,3-dimethyl-2-imidazolidinone is suggested.

The present inventors have already reported (JP application No. 11-311703) a method based on a completely new strategy for the safe production of a 5-phthalancarbonitrile compound, which method imposes a small environmental burden and utilizes a compound of the formula [III]

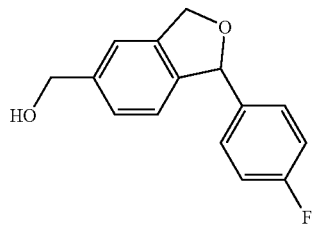

[III]

also referred to as compound [III]. They have now found that the compound [III], a key compound in this production method, can be produced easily from a compound of the formula [II]

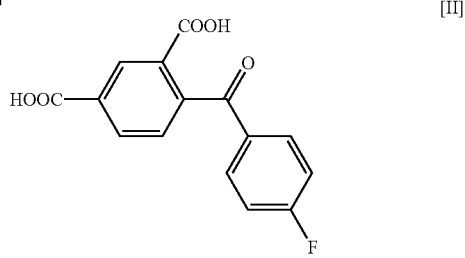

[II]

also referred to as compound [II], as a starting material. They have also found that compound [II] can be produced safely and with less burden on the environment by the independent use of 1,3-dimethyl-4-(4'-fluorobenzoyl)benzene (hereinafter to be also referred to as compound [I']), trimellitic anhydride or a novel compound of the formula [I]

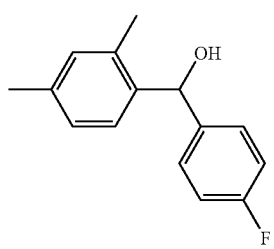

[I]

hereinafter to be referred to as compound [I], as the starting material. In addition, the present invention provides novel production methods of these starting materials.

Accordingly, the present invention relates to the following reactions.

Conversion of 4-bromofluorobenzene to 4-fluorophenyl-magnesium bromide, and reaction thereof with 2,4-dimethylbenzaldehyde to give compound [I].

Friedel-Crafts reaction of 4-fluorobenzoyl halide using m-xylene as a starting material and solvent to give compound [I'].

The following respective reactions (1) to (4) to give compound [II].
(1) Oxidation of compound [I].
(2) Friedel-Crafts reaction of 4-fluorobenzoyl halide using m-xylene as a starting material and solvent to give compound [I'], which is then subjected to oxidation.
(3) Friedel-Crafts reaction of 2,4-dimethylbenzoyl halide with fluorobenzene to give compound [I'], which is then subjected to oxidation.
(4) Friedel-Crafts reaction of trimellitic anhydride with fluorobenzene in a dichloro-substituted or trichloro-substituted benzene solvent.

The following respective reactions (1) and (2) to give compound [III].
(1) Reduction and cyclization of compound [II].
(2) Friedel-Crafts reaction of trimellitic anhydride with fluorobenzene to give a mixture of compound [II], an isomer thereof, and a compound of the formula [IV]

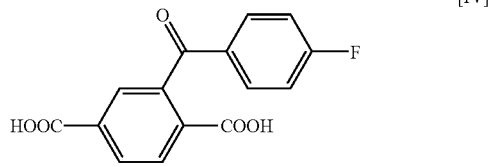

[IV]

hereinafter to be also referred to as compound [IV], which mixture is then subjected to reduction and cyclization, and then isolation.

Oxidation of compound [III] using manganese dioxide to give a compound of the formula [V]

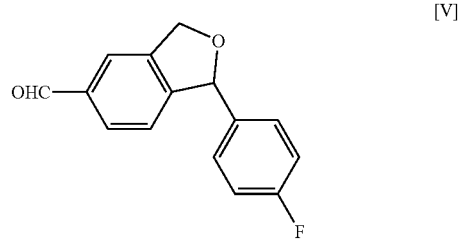

[V]

hereinafter to be also referred to as compound [V].

A reaction of compound [VI] with 3-(dimethylamino) propyl chloride in the presence of at least one of N,N,N', N'-tetramethylethylenediamine and 1,3-dimethyl-2-imidazolidinone and a condensing agent to give citalopram.

DETAILED DESCRIPTION OF THE INVENTION

The present invention is explained in detail in the following. In the present invention, by the reaction time is meant the period of time from the addition of all the reagents necessary for the reaction to the completion of the reaction.

Production Method of Compound [I]

The compound [I] is novel and can be produced by, for example, a Grignard reaction of 2,4-dimethylbenzaldehyde with a Grignard reagent of 4-bromofluorobenzene. To be specific, a Grignard reagent of 4-bromofluorobenzene is prepared in a reaction solvent, to which is added, preferably by dropwise addition, 2,4-dimethylbenzaldehyde to give compound [I]. The order of addition of the reaction reagents is subject to no particular limitation.

Production of the Grignard reagent of 4-bromofluorobenzene follows a conventional method, which includes, for example, dispersing metal magnesium in an organic solvent and dropwise addition of 4-bromofluorobenzene thereto generally at a temperature of from −30° C. to 100° C., preferably 15° C.–70° C. The amount of the metal magnesium to be used is that necessary for conversion of 4-bromofluorobenzene to a Grignard reagent, which is, for example, generally 0.9 mol–2 mol, preferably 0.95 mol–1.3 mol, per 1 mol of 4-bromofluorobenzene.

2,4-Dimethylbenzaldehyde is used in an amount of generally 0.5 mol–2 mol, preferably 0.8 mol–1.2 mol, per 1 mol of 4-bromofluorobenzene.

The reaction solvent in this reaction is subject to no particular limitation as long as it does not interfere with the Grignard reaction. A solvent which can be used for the preparation of a Grignard reagent can be applied to the Grignard reaction without isolation after preparation of the Grignard reagent, thereby preferably making the reaction step simple. Preferable solvent may be, for example, ether solvent (e.g., diethyl ether, diisopropyl ether, dibutyl ether, dipentyl ether, dihexyl ether, t-butyl methyl ether, ethylene glycol dimethyl ether, diethylene glycol dimethyl ether, triethylene glycol dimethyl ether, tetraethylene glycol dimethyl ether, tetrahydrofuran (THF), 1,4-dioxane, 1,3-dioxolan etc.) and the like, with more preference given to THF, diethyl ether, ethylene glycol dimethyl ether and diethylene glycol dimethyl ether. The amount of the reaction solvent to be used in this reaction is generally 1 L–30 L, preferably 2 L–20 L, per 1 kg of 4-bromofluorobenzene.

The temperature of this reaction is generally from −30° C. to 100° C., preferably from −10° C. to 50° C., and the reaction time is generally 5 min–6 hr. preferably 10 min–3 hr.

After inactivation of the Grignard reagent by the addition of water etc. to the reaction mixture, compound [I] can be isolated by a conventional method (e.g., extraction). After the isolation, it can be purified by a conventional method. Alternatively, it can be used in the next reaction without purification.

The compound [I] of the present invention may be present as an optically active compound or racemate due to an asymmetric carbon to which hydroxyl group is bonded. The racemate can be resolved into each optically active compound by a known method.

Production Method of Compound [I'] Using m-xylene as Starting Material

Method 1 (m-xylene as a Starting Material and Solvent)

As taught in U.S. Pat. No. 3,835,167, compound [I'] can be produced by Friedel-Crafts reaction of m-xylene with 4-fluorobenzoyl chloride. In this publication, dichloromethane is used as a solvent, which is unpreferable from the aspect of the influence on the environment. According to the present invention, a production method of compound [I'] at a high yield, which comprises the use of m-xylene as a starting material and solvent, is provided. That is, 4-fluorobenzoyl halide is subjected to Friedel-Crafts reaction using m-xylene as a starting material and solvent to give compound [I'] at a high yield, which route is desirable for the environment.

To be specific, Lewis acid or Brönsted acid is dispersed in m-xylene, and 4-fluorobenzoyl halide is added, preferably by dropwise addition, or Lewis acid or Brönsted acid is added, preferably by dropwise addition, to a solution of 4-fluorobenzoyl halide in m-xylene to give compound [I'] at a high yield.

The halide moiety of 4-fluorobenzoyl halide in Method 1 is subject to no particular limitation, and is exemplified by fluorine atom, chlorine atom, bromine atom and iodine atom, with preference given to chlorine atom.

In Method 1, the amount of m-xylene used as a starting material and solvent is generally 3 L–30 L, preferably 5 L–15 L, per 1 kg of 4-fluorobenzoyl halide.

The Lewis acid used in Method 1 is subject to no particular limitation as long as it is generally used for Friedel-Crafts reaction, and is exemplified by aluminum chloride, aluminum bromide, zinc fluoride, zinc chloride, zinc bromide, zinc iodide, boron trifluoride, boron trichloride, silicon tetrachloride, titanium tetrachloride and the like, with particular preference given to aluminum chloride in view of the quick reaction it affords. The amount of Lewis acid to be used is generally 2 mol–6 mol, preferably 3 mol–4 mol, per 1 mol of 4-fluorobenzoyl halide.

The Brönsted acid used in Method 1 is subject to no particular limitation as long as it is generally used for Friedel-Crafts reaction, and is exemplified by hydrogen fluoride, sulfuric acid, polyphosphoric acid, trifluoromethanesulfonic acid and the like, with preference given to trifluoromethanesulfonic acid. The amount of the Brönsted acid to be used is generally 0.0001 mol–1 mol, preferably 0.01 mol–0.2 mol, per 1 mol of 4-fluorobenzoyl halide.

In Method 1, the reaction temperature is generally from −20° C. to 120° C., preferably 10° C.–50° C., and the reaction time is generally 0.5 hr–15 hr, preferably 2 hr–8 hr.

The compound [II'] can be isolated and purified by a conventional method. For example, the reaction mixture is poured into hydrochloric acid and the organic layer obtained by separation is washed with water or aqueous alkali solution. The solvent is evaporated to isolate compound [I']. The isolated product can be further purified by a conventional method, or may be used in the next reaction without purification. By this method, an isomer of compound [I'], 1,4-dimethyl-2-(4'-fluorobenzoyl)benzene, is concurrently obtained, but can be easily separated by a conventional method such as recrystallization. The compound [I'] may be subjected to the next reaction without separation of the isomer.

Method 2 (Friedel-Crafts Reaction of 2,4-dimethylbenzoyl Halide with fluorobenzene)

The compound [I'] can be also produced by Friedel-Crafts reaction of 2,4-dimethylbenzoyl halide with fluorobenzene in a reaction solvent. The reaction solvent may be fluorobenzene (Method 2-1) or a solvent generally used for Friedel-Crafts reaction (Method 2-2). Specifically, in the case of Method 2-1, Lewis acid or Brönsted acid is dispersed in fluorobenzene and 2,4-dimethylbenzoyl halide is added, preferably added dropwise, or Lewis acid or Brönsted acid is added to a mixture of fluorobenzene and 2,4-dimethylbenzoyl halide, and in the case of Method 2-2, fluorobenzene is diluted in a solvent generally used for Friedel-Crafts reaction, Lewis acid or Brönsted acid is dispersed in this solution, and 2,4-dimethylbenzoyl halide is added, preferably added dropwise, or fluorobenzene and 2,4-dimethylbenzoyl halide are added to a solvent generally used for Friedel-Crafts reaction for dissolution and Lewis acid or Brönsted acid is added, to give compound [II] at a high yield.

The amount of fluorobenzene to be used in Method 2-1 is generally 2 L–20 L, preferably 4 L–10 L, per 1 kg of 2,4-dimethylbenzoyl halide.

The amount of fluorobenzene to be used in Method 2-2 is generally 1 mol–5 mol, preferably 1 mol–3 mol, per 1 mol of 2,4-dimethylbenzoyl halide.

The solvent generally used for Friedel-Crafts reaction in Method 2-2 is exemplified by methylene chloride, 1,2-dichloroethane, nitrobenzene, carbon disulfide and the like, with preference given to dichloro-substituted benzene and trichloro-substituted benzene from the aspect of the environment, with particular preference given to 1,2-dichlorobenzene. The amount of the reaction solvent to be used is generally 1 L–20 L, preferably 5 L–15 L, per 1 kg of 2,4-dimethylbenzoyl halide.

The Lewis acid to be used in Method 2-1 and Method 2-2 is subject to no particular limitation as long as it is generally used for Friedel-Crafts reaction, and is exemplified by aluminum chloride, aluminum bromide, zinc fluoride, zinc chloride, zinc bromide, zinc iodide, boron trifluoride, boron trichloride, silicon tetrachloride, titanium tetrachloride and the like, with preference given to aluminum chloride in view of the quick reaction it provides. The amount of the Lewis acid to be used is generally 0.8 mol–3 mol, preferably 1 mol–1.5 mol, per 1 mol of 2,4-dimethylbenzoyl halide.

The Brönsted acid used in Method 2-1 and Method 2-2 is subject to no particular limitation as long as it is generally used for Friedel-Crafts reaction, and is exemplified by hydrogen fluoride, sulfuric acid, polyphosphoric acid, trifluoromethanesulfonic acid and the like, with preference given to trifluoromethanesulfonic acid. The amount of the Brönsted acid to be used is generally 0.0001 mol–1 mol, preferably 0.01 mol–0.5 mol, per 1 mol of 2,4-dimethylbenzoyl halide.

In Method 2-1 and Method 2-2, the reaction temperature is generally from −20° C. to 100° C., preferably 0° C.–90° C., and the reaction time is generally 0.5 hr–10 hr, preferably 1 hr–4 hr.

The compound [I'] can be isolated and purified by a conventional method. For example, the reaction mixture is poured into hydrochloric acid and the organic layer obtained by separation is washed with water or aqueous alkali solution. The solvent is evaporated to isolate compound [I'].

Production Method of Compound [II]

Method A (Production Method of Compound [II] from Compound [I] as Starting Material)

The compound [II] can be obtained by oxidation of novel compound [I]. The oxidation of compound [I] is performed using, for example, an oxidizing agent. To be specific, a solution of compound [I] and a solution or dispersion of the oxidizing agent are mixed and stirred to give compound [II]. The solvent for these solution and dispersion is exemplified by the following reaction solvents.

As regards Method A, the oxidizing agent is subject to no particular limitation as long as it allows oxidation of methyl and hydroxyl into carboxyl and carbonyl, respectively. Examples of the oxidizing agent include permanganate, dichromate and the like. Considering the influence on the environment and toxicity, permanganate (e.g., potassium permanganate and the like) is preferable. While permanganate used for oxidation reaction causes side production of manganese dioxide, manganese dioxide can be used as an oxidizing agent for synthesis of compound [V] from compound [III] to be mentioned later. Therefore, manganese dioxide is preferably used because it does not need to be wasted and can reduce the production cost. The amount of the oxidizing agent to be used in Method A is generally 3 mol–15 mol, preferably 4.6 mol–10 mol, more preferably 6 mol–7.5 mol, per 1 mol of compound [I].

In Method A, the reaction solvent is subject to no particular limitation as long as it is hardly oxidized by the oxidizing agent to be used for the oxidation reaction. Examples thereof include water, t-butyl alcohol, t-amyl alcohol, acetone, ethyl methyl ketone, isobutyl methyl ketone, methylene chloride, chloroform, 1,2-dichloroethane, benzene, monochlorobenzene, 1,2-dichlorobenzene, acetic acid, propionic acid, butyric acid and the like, and mixed solvents thereof, with preference given to water, t-butyl alcohol, a mixed solvent of water and t-butyl alcohol, t-amyl alcohol, a mixed solvent of water and t-amyl alcohol, acetone and a mixed solvent of water and acetone. The amount of the solvent to be used is generally 5 L–50 L, preferably 8 L–24 L, per 1 kg of compound [I].

In Method A, the reaction temperature is generally 0° C.–120° C., preferably 50–100° C., and the reaction time is generally 0.5 hr–12 hr, preferably 2 hr–8 hr.

The compound [II] can be isolated by a conventional method. For example, the reaction mixture is filtrated to remove insoluble matter (inclusive of manganese dioxide), a typical inorganic acid (e.g., hydrochloric acid, sulfuric acid etc.) is added and the precipitated compound [II] is collected by filtration. After the isolation, it is further purified by a conventional method. Alternatively, it can be used in the next reaction without purification.

Method B (Production Method of Compound [II] Using Compound [I'] as Starting Material)

The compound [II] can be also obtained by oxidation of compound [I'], wherein the oxidation can be performed by the use of an oxidizing agent. In Method B, the amount of the oxidizing agent to be used is generally 2.5 mol–14 mol, preferably 4 mol–9 mol, more preferably 5.5 mol–7 mol, per 1 mol of compound [I'], and the amount of the solvent to be used is generally 5 L–50 L, preferably 8 L–24 L, per 1 kg of compound [I']. Other factors such as reaction conditions, isolation conditions and the like are the same as those employed for the oxidation reaction in the above-mentioned Method A. The isolated product can be purified by a conventional method. Alternatively, it can be used in the next reaction without purification.

Method C (Production Method of Compound [II] Using trimellitic anhydride as Starting Material)

U.S. Pat. No. 3,835,167 teaches Friedel-Crafts reaction of trimellitic anhydride and benzene. According to the method disclosed in this publication, nitrobenzene is used as a solvent, which is unpreferable from the aspect of the environment. According to the present invention, the reaction in this publication is carried out using fluorobenzene instead of benzene and under the same conditions or at a higher temperature, whereby the progress of the Friedel-Crafts reaction is mostly prevented (see Comparative Example 1). The present inventors have studied a solvent that allows smooth progress of the Friedel-Crafts reaction of trimellitic anhydride and fluorobenzene, and that is environmentally preferable, and found dichloro-substituted benzene and trichloro-substituted benzene to be most suitable. That is, trimellitic anhydride and fluorobenzene are subjected to Friedel-Crafts reaction in a dichloro-substituted or trichloro-substituted benzene solvent to give compound [II] environmentally preferably and smoothly.

To be specific, trimellitic anhydride and fluorobenzene are dispersed in a reaction solvent, Lewis acid or Brönsted acid is added and the mixture is stirred to give compound [II].

In Method C, the amount of fluorobenzene to be used is generally 1 mol–10 mol, preferably 1.2 mol–3 mol, per 1 mol of trimellitic anhydride.

The reaction solvent in Method C, dichloro-substituted or trichloro-substituted benzene, may be, for example, 1,2-dichlorobenzene, 1,3-dichlorobenzene, 1,2,4-trichlorobenzene, 1,2,3-trichlorobenzene and the like, with particular preference given to 1,2-dichlorobenzene because it produces compound [II] relatively highly selectively. These solvents may be used alone or in combination. The amount of the reaction solvent to be used is generally 5 L–40 L, preferably 10 L–25 L, per 1 kg of trimellitic anhydride. Other than the above-mentioned solvents, certain solvents can accelerate the reaction in Method C. Examples thereof include methylene chloride, 1,2-dichloroethane, nitrobenzene, carbon disulfide and the like, with preference given to methylene chloride and 1,2-dichloroethane. The amount of the solvent to be used is 4 L–40 L, preferably 8 L–25 L, per 1 kg of trimellitic anhydride.

In Method C, the Lewis acid is subject to no particular limitation as long as it is used for Friedel-Crafts reaction. Examples thereof include aluminum chloride, aluminum bromide, zinc fluoride, zinc chloride, zinc bromide, zinc iodide, boron trifluoride, boron trichloride, silicon tetrachloride, titanium tetrachloride and the like, with particular preference given to aluminum chloride in view of the quick reaction it provides. The amount of the Lewis acid to be used is generally 2.5 mol–5 mol, preferably 3 mol–3.5 mol, per 1 mol of trimellitic anhydride.

The Brönsted acid used in Method C is subject to no particular limitation as long as it is generally used for Friedel-Crafts reaction, and is exemplified by hydrogen fluoride, sulfuric acid, polyphosphoric acid, trifluoromethanesulfonic acid and the like, with preference given to trifluoromethanesulfonic acid. The amount of the Brönsted acid to be used is 0.0001 mol–1 mol, preferably 0.01 mol–0.2 mol, per 1 mol of trimellitic anhydride.

In Method C, the reaction temperature is generally 40° C.–150° C., preferably 70° C.–120° C., and the reaction time is generally 0.5 hr–16 hr, preferably 2 hr–9 hr.

In Method C, compound [II] is obtained as a mixture with its isomer, compound [IV]. This mixture can be easily separated from the reaction mixture according to a conventional method. For example, the reaction mixture is poured into an acidic aqueous solution such as aqueous hydrochloric acid solution, aqueous sulfuric acid solution and the like and partitioned to separate an organic layer, which is, after extraction with an aqueous alkali solution, neutralized with an acidic aqueous solution to separate the mixture. The compound [II] and compound [IV] can be separated by recrystallization and the like. The mixture can be used in the next reaction without separation of compound [II] from compound [IV]. The mixture and compound [II] can be used in the next reaction without purification.

Production Method of Compound [III]

The compound [III] has been disclosed in JP Application No. 11-311703 by the present inventors as an important intermediate for efficient synthesis of compound [VI] which is a citalopram precursor. The present inventors have studied a method for producing compound [III] by a new route and found compound [II] to be a precursor of compound [III], as well as a simple and easy production method of compound [III] from compound [II]. That is, compound [III] can be easily obtained by reduction and cyclization of compound [II]. The order of the reduction and cyclization is subject to no particular limitation. Cyclization after reduction of compound [II], or cyclization after partial reduction (reduction of ketone) of compound [II], followed by reduction may be employed. Cyclization after reduction is preferable because it requires a short reaction step. The starting material compound [II] can be used as a mixture with an isomer, compound [IV], for the production of compound [III]. When the mixture of compound [II] and compound [IV] is subjected to reduction and cyclization, compound [III] is obtained along with the isomer of compound [III]. When compared with the yield of compound [III] when it is obtained by isolation followed by reduction and cyclization, the yield is higher by the former route. Therefore, isolation not in the stage of compound [II] but in the stage of compound [III] is efficient and preferable.

The compound obtained by reduction of compound [II] is represented by the formula [VII]

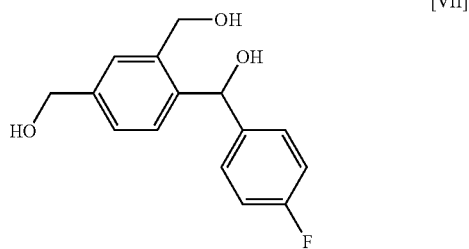

[VII]

hereinafter to be also referred to as compound [VII]. When cyclization is conducted after partial reduction of compound [II], and further reduction is applied, various intermediates are present, such as a compound of the formula

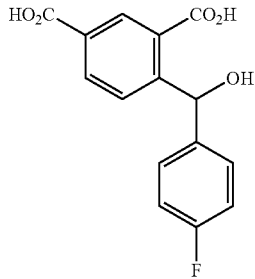

and the like. The production of compound [III] from compound [II] in the present invention consists of two steps of (1) reduction and (2) cyclization.

When cyclization follows reduction, the reaction conditions of (1) may lead to the simultaneous production of compound [VII] and compound [III], in which case (2) can be omitted depending on the proportion of compound [III] produced.

The following explains a method for producing compound [III] by cyclization after reduction of compound [II].

The Conditions of (1) are as Follows.

The compound [II] can be reduced in the same manner as in the generally known reduction of carboxylic acid into alcohol by the use of a reducing agent. To be specific, a reducing agent is dispersed in a reaction solvent, and compound [II] is added to the dispersion, preferably by dropwise addition to give compound [VII]. This reduction is preferably conducted using a suitable catalyst in addition to the reducing agent. The catalyst is preferably added after the addition of a reducing agent and compound [II].

The reducing agent in (1) is subject to no particular limitation as long as it is generally used for the conversion of carboxylic acid to alcohol. Examples thereof include sodium borohydride, lithium aluminum hydride, sodium bis(2-methoxyethoxy)aluminum hydride, borane-THF complex, borane-dimethyl sulfide complex and the like, with preference given to sodium borohydride. The amount of the reducing agent to be used is generally 1.25 mol–7.5 mol, preferably 2.5 mol–5 mol, per 1 mol of compound [II].

The catalyst in (1) is exemplified by inorganic acid (e.g., hydrochloric acid, sulfuric acid, phosphoric acid, boric acid, nitric acid etc.), organic acid (e.g., methanesulfonic acid, trifluoromethanesulfonic acid, p-toluenesulfonic acid, benzenesulfonic acid etc.), Lewis acid (e.g., boron trifluoride, boron trichloride, boron tribromide, zinc fluoride, zinc chloride, zinc bromide, zinc iodide, aluminum fluoride, aluminum chloride, aluminum bromide, magnesium fluoride, magnesium chloride, magnesium bromide, magnesium iodide, silicon tetrachloride, titanium tetrachloride etc.), dialkyl sulfate (e.g., dimethyl sulfate, diethyl sulfate etc.) and the like, with preference given to Lewis acid and dialkyl sulfate in view of an increased yield and selectivity, with more preference given to sulfuric acid, boron trifluoride, dimethyl sulfate and diethyl sulfate for higher yield. The amount of the catalyst to be used is generally 1.25 mol–7 mol, preferably 2 mol–6 mol, per 1 mol of compound [II].

The reaction solvent in (1) is subject to no particular limitation as long as it hardly shows reaction under the conditions of reduction. Preferred are ether solvents. Examples of the ether solvent include diethyl ether, diisopropyl ether, dibutyl ether, dipentyl ether, dihexyl ether, t-butyl methyl ether, ethylene glycol dimethyl ether, diethylene glycol dimethyl ether, triethylene glycol dimethyl ether, tetraethylene glycol dimethyl ether, tetrahydrofuran (THF), 1,4-dioxane, 1,3-dioxolan and the like, with preference given to THF, diethyl ether, ethylene glycol dimethyl ether, diethylene glycol dimethyl ether, t-butyl methyl ether, dibutyl ether and the like, and with particular preference given to THF, t-butyl methyl ether, dibutyl ether, ethylene glycol dimethyl ether and diethylene glycol dimethyl ether. The amount of the reaction solvent to be used is generally 1 L–40 L, preferably 5 L–20 L, per 1 kg of compound [II].

In (1), trialkyl borate (e.g., trimethyl borate, triethyl borate, tripropyl borate, tributyl borate etc.) is preferably used to prevent gelation of the reaction mixture. The amount of trialkyl borate to be used is preferably 0.1 mol–3 mol, more preferably 0.1 mol–0.5 mol, per 1 mol of compound [II].

In (1), the reaction temperature is generally from −20° C. to 120° C., preferably 25° C.–75° C., and the reaction time is generally 0.5 hr–10 hr, preferably 2 hr–7 hr.

The compound [VII] can be isolated and purified by a conventional method. For example, water is added to the obtained reaction mixture, and the mixture is cooled to allow crystal precipitation. The reaction mixture containing compound [VII] can be used in the next reaction as it is without isolation of compound [VII]. Alternatively, a reaction mixture wherein the reducing agent has been inactivated with water can be used in the reaction.

The Following Explains (2).

Cyclization of compound [VII] is conducted via dehydration reaction by applying a heat. In this case, for acceleration of the dehydration reaction, further addition of an acid catalyst is preferable. To be specific, for example, an acid catalyst is added to the reaction mixture obtained in (1) or a mixture of the reaction solvent and compound [VII], to give compound [III].

The acid catalyst in (2) is exemplified by inorganic acid (e.g., hydrochloric acid, sulfuric acid, phosphoric acid, polyphosphoric acid, boric acid, nitric acid etc.), organic acid (e.g., acetic acid, propionic acid, trifluoroacetic acid, methanesulfonic acid, trifluoromethanesulfonic acid, p-toluenesulfonic acid, benzenesulfonic acid, benzoic acid etc.), Lewis acid (e.g., boron trifluoride, boron trichloride, boron tribromide, zinc fluoride, zinc chloride, zinc bromide, zinc iodide, aluminum fluoride, aluminum chloride, aluminum bromide, magnesium fluoride, magnesium chloride, magnesium bromide, magnesium iodide, silicon tetrachloride, titanium tetrachloride and the like) and the like, with preference given to inorganic acid, particularly preferably hydrochloric acid, sulfuric acid and phosphoric acid. The amount of the acid catalyst to be used is generally 0.01 kg-50 kg, preferably 0.1 kg-5 kg, per 1 kg of compound [II] which is a starting material in (1).

The cyclization reaction tends to proceed easily by the addition of the above-mentioned acid catalyst. The use of the above-mentioned acid catalyst in (1) often advances not only the reduction reaction but also cyclization reaction. Thus, the use in (1) of an excess acid catalyst mentioned above enables synthesis of compound [III] in one pot. In this case, the amount of catalyst to be used in (1) is generally 2 mol–30 mol, preferably 3 mol–15 mol, per 1 mol of compound [II] which is a starting material in (1).

The solvent in (2) is subject to no particular limitation as long as it does not interfere with the reaction. Preferred are the solvents used in (1), and a mixed solvent of the solvent used in (1) and water. The use of such solvents is preferable because the obtained reaction mixture can be applied to the step of (2) after the completion of the reaction of (1) without isolation of compound [VII] from the reaction mixture, and the reaction mixture containing water to inactivate the reducing agent after the completion of the reaction of (1) can be applied as it is to the step of (2), which means that the isolation and purification of compound [VII] can be omitted. When water is added to inactivate the reducing agent, only the solvent used for the reaction mixture of (1) can be evaporated to leave only water, which is subjected to the cyclization reaction, or a suitable solvent other than the solvent used in (1) may be added to the above-mentioned mixture containing only water. Examples of the suitable solvent other than the solvent used in (1) is subject to no particular limitation. Examples thereof include hydrocarbon solvents (e.g., toluene, xylene, mesitylene, hexane, heptane, octane etc.) and the like. The amount thereof is generally 0.5 L–20 L, preferably 3 L–10 L, per 1 kg of compound [II] which is a starting material in (1).

In (2), the reaction time is generally 0.5 hr–15 hr, preferably 1 hr–7 hr, and the reaction temperature is generally 10° C.–100° C., preferably 20° C.–70° C.

The compound [III] can be isolated by a conventional method, for example, by adding water to the reaction mixture, cooling the mixture and collecting the resulting crystals. After the isolation, compound [III] can be further purified by a conventional method. Alternatively, it can be used in the next reaction without purification.

A method comprising cyclization after partial reduction of compound [II] and further reduction, is performed in the same manner as in the above-mentioned method by the use of reaction reagents (e.g., reducing agent) generally used for desired partial reduction and cyclization.

Production Method of Compound [V]

The compound [V] is useful as an intermediate for the efficient synthesis of compound [VI] which is a precursor of citalopram. The method for efficient synthesis of compound [V] is important because it eventually contributes greatly to the efficient synthesis of citalopram. It is known that compound [V] can be obtained by oxidation using compound [III] as an oxidizing agent (JP application No. 11-311703). The positions of compound [III] that are easily oxidized are 5-position hydroxymethyl of 1,3-dihydroisobenzofuran ring, and the 1-position and 3-position carbons. Therefore, oxidation of compound [III] may result in the oxidation of the 1-position and 3-position carbons besides the 5-position hydroxymethyl. After intensive studies, the present inventors have found that the use of manganese dioxide as an oxidizing agent results in the production of compound [V] at a high yield almost without any side reaction (oxidation of the 1-position and 3-position carbons). That is, by the use of manganese dioxide as an oxidizing agent for the oxidation of compound [III], compound [V] can be obtained at a high yield. To be specific, compound [III] is dissolved or dispersed in a suitable solvent and manganese dioxide is added to give compound [V]. The order of addition and the like are subject to no particular limitation.

The amount of the manganese dioxide to be used for this reaction is generally 1 kg-20 kg, preferably 3 kg-10 kg, per 1 kg of compound [III].

The solvent to be used for this reaction is subject to no particular limitation as long as it is not easily subject to oxidation, and is exemplified by ethers (e.g., diethyl ether, diisopropyl ether, dibutyl ether, dipentyl ether, dihexyl ether, t-butyl methyl ether, ethylene glycol dimethyl ether, diethylene glycol dimethyl ether, triethylene glycol dimethyl ether, tetraethylene glycol dimethyl ether, tetrahydrofuran (THF), 1,4-dioxane, 1,3-dioxolan etc.), ketones (e.g., acetone, methyl ethyl ketone, methyl isobutyl ketone, 2-pentanone, 3-pentanone, cyclopentanone, cyclohexanone etc.), esters (e.g., ethyl acetate, propyl acetate, isopropyl acetate, butyl acetate, isobutyl acetate, amyl acetate, isoamyl acetate, benzyl acetate, phenyl acetate, methyl propionate, ethyl propionate, propyl propionate, isopropyl propionate, butyl propionate, isobutyl propionate, amyl propionate, isoamyl propionate, benzyl propionate, phenyl propionate, methyl butyrate, ethyl butyrate, propyl butyrate, isopropyl butyrate, butyl butyrate, isobutyl butyrate, amyl butyrate, isoamyl butyrate, benzyl butyrate, phenyl butyrate etc.), lactones (e.g., γ-butyrolactone etc.), carbonates (e.g., dimethyl carbonate, diethyl carbonate, ethylene carbonate etc.), aromatic hydrocarbons (e.g., benzene, toluene, xylene, mesitylene, ethylbenzene, t-butylbenzene etc.), aliphatic hydrocarbons (e.g., pentane, hexane, isohexane, heptane, isoheptane, octane, isooctane, nonane, decane, undecane, dodecane, petroleum ether etc.), halogen substituted aromatic hydrocarbons (e.g., monochlorobenzene, 1,2-dichlorobenzene, 1,3-dichlorobenzene, 1,2,4-trichlorobenzene, 1,2,3-trichlorobenzene etc.), halogen substituted aliphatic hydrocarbons (e.g., dichloromethane, chloroform, 1,2-dichloroethane, 1,1,2-trichloroethane, 1,1,1-trichloroethane, 1-chloropropane, 2-chloropropane etc.), amide solvents (e.g., N,N-dimethylformamide, N,N-dimethylacetamide, N-methylpyrrolidone etc.), sulfur-containing solvents (e.g., dimethyl sulfoxide, sulforane etc.), and the like. Of these, particularly preferable solvents are t-butyl methyl ether, ethylene glycol dimethyl ether, diethylene glycol dimethyl ether, toluene, xylene, mesitylene, dichloromethane and monochlorobenzene. The amount of the solvent to be used is generally 3 L–50 L, preferably 5 L–20 L, per 1 kg of compound [III].

In this reaction, the reaction temperature is generally from −10° C. to 100° C., preferably 10° C.–60° C., and the reaction time is generally 0.1 hr–24 hr, preferably 0.5 hr–5 hr.

The compound [V] can be isolated by a conventional method comprising, for example, filtration of the reaction mixture, and evaporation of the solvent from the obtained filtrate. After filtration of the reaction mixture, it can be used in the next reaction without evaporation of the solvent from the resulting filtrate. The waste manganese compound thus filtered off can be reprocessed and recycled for use as permanganate or manganese dioxide by a conventional method, which is environmentally preferable.

Production Method of Compound [VI]

The compound [VI] is a useful intermediate as a precursor of citalopram. The compound [VI] can be obtained by successive oxidation, oximation (condensation with hydroxylamine or a mineral acid salt thereof) and dehydration of compound [III] as a starting compound. When the following solvents are used, the series of reactions (oxidation, oximation and dehydration reaction) can be conducted in a single solvent and compound [VI] can be produced easily and efficiently because evaporation of the solvent can be omitted. To be specific, compound [III] and an oxidizing agent are added to the following solvent to allow oxidation reaction. After the completion of the oxidation reaction, the oxidizing agent is filtered off and hydroxylamine or a mineral acid salt thereof is added to the resulting filtrate to allow oximation reaction. Finally, a dehydrating agent is added to the obtained reaction mixture for a dehydration reaction to give compound [VI].

The solvent usable for oxidation, oximation and dehydration reaction is subject to no particular limitation as long as it does not interfere with each reaction and is exemplified by ethers (e.g., dibutyl ether, dipentyl ether, dihexyl ether, diethylene glycol dimethyl ether, triethylene glycol dimethyl ether, tetraethylene glycol dimethyl ether etc.), ketones (e.g., cyclopentanone, cyclohexanone etc.), esters (e.g., amyl acetate, isoamyl acetate, benzyl acetate, phenyl acetate, butyl propionate, isobutyl propionate, amyl propionate, isoamyl propionate, benzyl propionate, phenyl propionate, butyl butyrate, isobutyl butyrate, amyl butyrate, isoamyl butyrate, benzyl butyrate, phenyl butyrate etc.), lactones (e.g., γ-butyrolactone etc.), carbonates (e.g., diethyl carbonate, ethylene carbonate etc.), aromatic hydrocarbons (e.g., xylene, mesitylene, ethylbenzene, t-butylbenzene, toluene etc.), halogen substituted aromatic hydrocarbons (e.g., monochlorobenzene, 1,2-dichlorobenzene, 1,3-dichlorobenzene, 1,2,4-trichlorobenzene, 1,2,3-trichlorobenzene etc.), amide solvents (e.g., N,N-dimethylformamide, N,N-dimethylacetamide, N-methylpyrrolidone etc.), sulfur-containing solvents (e.g., dimethyl sulfoxide, sulforane etc.), and the like. Of these, particularly preferable solvents are diethylene glycol dimethyl ether, xylene, mesitylene, toluene, t-butylbenzene and monochlorobenzene. The amount of the solvent to be used is generally 3 L–50 L, preferably 5 L–20 L, per 1 kg of compound [III], the starting material.

The Following Explains the Oxidation Reaction of Compound [III].

The compound [III] can be oxidized in completely the same manner as in the above-mentioned "Production method of compound [V]" except the solvent is other than those mentioned above. The compound [V] obtained by oxidation of compound [III] can be used in the next oximation reaction without isolation from the reaction mixture.

Note that the oxidizing agent should be removed from the reaction mixture according to a conventional method.

The Following Explains the Oximation Reaction.

The compound [V] can be converted to an oxime by, for example, oximation reaction with hydroxylamine or a mineral acid salt thereof. To be specific, for example, the oxidizing agent is filtered off from the reaction mixture after oxidation, and hydroxylamine or a mineral acid salt thereof is added to give the oxime.

Examples of hydroxylamine mineral acid salt include salts of hydroxylamine with hydrochloric acid, sulfuric acid, phosphoric acid, nitric acid and the like, with preference given to hydroxylamine hydrochloride and hydroxylamine sulfate.

The amount of hydroxylamine or a mineral acid salt thereof to be used for oximation is generally 1 mol–5 mol, preferably 1 mol–2 mol, per 1 mol of compound [III] used in the oxidation step.

When a hydroxylamine mineral acid salt is used, a suitable base is preferably added in 1 mol–5 mol per 1 mol of hydroxylamine mineral acid salt. The base is added, preferably dropwise, together with hydroxylamine mineral acid salt or after the addition thereof. The base is subject to no particular limitation as long as it shows less influence on cyano group. Examples thereof include organic base (e.g., triethylamine, tributylamine, dimethylaniline, pyridine, sodium methoxide, sodium ethoxide, sodium t-butoxide, potassium t-butoxide etc.), inorganic base (e.g., sodium carbonate, sodium hydrogencarbonate, sodium hydroxide, potassium carbonate, potassium hydrogencarbonate, potassium hydroxide etc.) and the like, with preference given to triethylamine.

The reaction temperature of the oximation reaction is generally 20° C.–120° C., preferably 40° C.–100° C., and the reaction time is generally 10 min–4 hr, preferably 30 min–2 hr.

The oxime obtained from compound [III] can be subjected to dehydration reaction without isolation from the reaction mixture.

The Following Explains Dehydration Reaction.

The oxime obtained by oximation reaction can be dehydrated by the use of a dehydration agent. For example, a dehydration agent is added to the reaction mixture after the oximation reaction to give compound [VI].

Examples of the dehydration agent to be used for this dehydration step include anhydride (e.g., acetic anhydride, phthalic anhydride etc.), phosphorus oxychloride, methanesulfonyl chloride, p-toluenesulfonyl chloride and the like, with particular preference given to acetic anhydride in view of the environment and yield. The amount of the dehydration agent to be used is generally 1 mol–10 mol, preferably 2 mol–5 mol, per 1 mol of oxime.

In the dehydration reaction, the reaction temperature is generally 60° C.–160° C., preferably 120° C.–150° C., more preferably 125° C.–150° C., and the reaction time is generally 0.5 hr–8 hr, preferably 1.5 hr–6 hr.

The compound [VI] can be isolated by subjecting the reaction mixture to a conventional method (e.g., neutralization, extraction, crystallization and the like).

Production Method of Citalopram

Citalopram can be obtained at a high yield by reacting compound [VI] with 3-(dimethylamino)propyl chloride together with a condensing agent and in the presence of at least one of N,N,N',N'-tetramethylethylenediamine and 1,3-dimethyl-2-imidazolidinone. To be specific, compound [VI], 3-(dimethylamino)propyl chloride, a condensing agent, and at least one of N,N,N',N'-tetramethylethylenediamine and 1,3-dimethyl-2-imidazolidinone are mixed in a suitable solvent, and the mixture is heated where necessary for the progress of the reaction to give citalopram. The order of addition is subject to no particular limitation. For example, compound [VI] is added to the reaction solvent, and a condensing agent and 3-(dimethylamino)propyl chloride are successively added. Alternatively, compound [VI] and 3-(dimethylamino)propyl chloride are added to the reaction solvent, and a condensing agent is added, or a condensing agent is added to the reaction solvent, and compound [VI] and 3-(dimethylamino)propyl chloride are successively added or added by mixture. In this case, N,N,N',N'-tetramethylethylenediamine and 1,3-dimethyl-2-imidazolidinone can be added at any stage, but they are preferably divided and added before and after the addition of the condensing agent for easy progress of the reaction. To be specific, compound [VI] is added to the reaction solvent and 3-(dimethylamino)propyl chloride, N,N,N'-N'-tetramethylethylenediamine (or 1,3-dimethyl-2-imidazolidinone), condensing agent and N,N,N',N'-tetramethylethylenediamine (or 1,3-dimethyl-2-imidazolidinone) are successively added. The reagents used in the present invention can be added as they are or added after dilution with a reaction solvent or a different solvent that does not interfere with the reaction (e.g., triethylamine, pyridine, N,N-dimethylaniline and the like).

In the present invention, a quaternary ammonium salt (e.g., tetra n-butylammonium halide, benzyltrialkylammonium halide and the like) is added to the reaction system to carry out the reaction without elevating the reaction temperature too high. The amount of the quaternary ammonium salt to be added is preferably 0.001 mol–0.1 mol, more preferably 0.01 mol–0.05 mol, per 1 mol of compound [VI].

The amount of 3-(dimethylamino)propyl chloride to be added is preferably 1 mol–3 mol, more preferably 1 mol–1.5 mol, per 1 mol of compound [VI]. When the 3-(dimethylamino)propyl chloride is in the form of a hydrochloride, it is preferably prepared into a free form by neutralization, and used for the reaction of the present invention.

The amount of N,N,N',N'-tetramethylethylenediamine to be added is preferably 0.1 mol–10 mol, more preferably 0.2 mol–4 mol, per 1 mol of compound [VI].

The amount of 1,3-dimethyl-2-imidazolidinone to be added is preferably 1 mol–50 mol, more preferably 3 mol–30 mol, per 1 mol of compound [VI].

The condensing agent used for the production of citalopram is subject to no particular limitation as long as it is generally used as a condensing agent. Examples thereof include sodium hydride, potassium hydride, calcium hydride, potassium hydroxide, sodium hydroxide, potassium carbonate, sodium carbonate, potassium t-butoxide, sodium t-butoxide, sodium methoxide, sodium ethoxide, potassium methoxide, potassium ethoxide, lithium diisopropylamide, lithium hexamethyldisiladide and the like, with preference given to sodium hydride and potassium t-butoxide, with more preference given to sodium hydride. The amount of the condensing agent to be used is generally 0.9 mol–3 mol, preferably 1 mol–1.5 mol, per 1 mol of compound [VI].

The reaction solvent to be used for the production of citalopram is, for example, dimethyl sulfoxide, sulfolane, N,N-dimethylformamide, N,N-dimethylacetamide, tetrahydrofuran (THF), 1,4-dioxane, 1,3-dioxolan, dimethoxyethane, diethylene glycol dimethyl ether, t-butyl methyl ether, diethyl ether, diisopropyl ether, dibutyl ether, anisole, benzene, toluene, xylene, mesitylene, cyclohexane, heptane, hexane, liquid paraffin and the like, with preference given to dimethyl sulfoxide, sulforane, N,N-dimethylformamide, N,N-dimethylacetamide, THF, 1,3-dioxolan, dimethoxyethane, diethylene glycol dimethyl ether, toluene, xylene, t-butyl methyl ether and liquid paraffin, which may be used alone or in combination. In addition, N,N,N',N'-tetramethylethylenediamine and 1,3-dimethyl-2-imidazolidinone may be used as a reaction solvent. The reaction solvent in the present invention is particularly preferably a mixed solvent of toluene and N,N,N',N'-tetramethylethylenediamine or 1,3-dimethyl-2-imidazolidinone for a higher yield.

The amount of the reaction solvent to be used for the production of citalopram varies depending on the kind of the reaction solvent, reaction conditions and the like. It is generally preferably 1 L–100 L, more preferably 3 L–30 L, per 1 kg of compound [VI].

The reaction temperature for the production of citalopram is generally from −70° C. to 150° C., preferably 20° C.–90° C., more preferably 40° C.–70° C. The reaction time is subject to no particular limitation, and is generally 30 min–15 hr, preferably 2 hr–8 hr.

Citalopram can be isolated and purified generally by a post-treatment and separation. For example, the reaction mixture is poured into ice water and extracted with an organic solvent. The obtained organic layer is extracted with an aqueous acid solution, neutralized and extracted again with an organic solvent, which is followed by evaporation of the solvent to isolate citalopram. Where necessary, a conventional method is used for the purification.

The present invention is explained in detail by referring to illustrative examples. The present invention is not limited by these examples in any way.

EXAMPLE 1

Synthesis of (2,4-dimethylphenyl)-(4'-fluorophenyl)methanol (Compound [I])

Under a nitrogen atmosphere, turnings of magnesium (16.8 g) were dispersed in THF (116 ml), and iodine (0.1 g) was added. Under a nitrogen atmosphere, a solution of 4-bromofluorobenzene (116 g) in THF (201 ml) was added dropwise at 15–40° C., and the mixture was stirred at 20–40° C. for 2 hr. The obtained mixture with a Grignard reagent was cooled and thereto was added dropwise a solution of 2,4-dimethylbenzaldehyde (81 g) in THF (81 ml) at 0–20° C. After the dropwise addition, the reaction mixture was stirred at 0–20° C. for 2 hr. A saturated aqueous ammonium chloride solution was added to stop the reaction. The reaction mixture was partitioned and the obtained organic layer was retained. The aqueous layer was extracted with toluene and combined with the organic layer obtained earlier, and washed with saturated brine. The solvent was evaporated from the organic layer under reduced pressure to give (2,4-dimethylphenyl)-(4'-fluorophenyl)methanol (139.2 g, 100%) as a colorless oil.

$^1$H-NMR(CDCl$_3$, 400 MHz) δ=2.05(1H,d,J=4 Hz), 2.21(3H,s), 2.31(3H,s), 5.96(1H,d,J=4 Hz), 6.98(1H,s), 7.00(2H,t,J=9 Hz), 7.05(1H,d,J=8 Hz), 7.29(2H,dd,J=9 Hz,J=5 Hz), 7.33(1H,d,J=8 Hz) ppm

EXAMPLE 2

Synthesis of (2,4-dimethylphenyl)-(4'-fluorophenyl)methanol (Compound [I])

Under a nitrogen atmosphere, turnings of magnesium (16.8 g) were dispersed in THF (54 ml), and iodine (0.1 g) was added. Under a nitrogen atmosphere, a solution of 4-bromofluorobenzene (116 g) in THF (201 ml) was added dropwise at 15–40° C., and the mixture was stirred at 20–40° C. for 2 hr. The obtained mixture with a Grignard reagent was cooled and thereto was added dropwise a solution of 2,4-dimethylbenzaldehyde (81 g) in THF (81 ml) at 0–20° C. After the dropwise addition, the reaction mixture was stirred at 0–20° C. for 2 hr. A saturated aqueous ammonium chloride solution was added to stop the reaction. The reaction mixture was partitioned and the obtained organic layer was washed with saturated brine. The solvent was evaporated from the organic layer under reduced pressure to give (2,4-dimethylphenyl)-(4'-fluorophenyl)methanol (139.2 g, 100%) as a colorless oil. The obtained colorless oil was measured for $^1$H-NMR and found to be the same as in Example 1.

EXAMPLE 3

Synthesis of (2,4-dimethylphenyl)-(4'-fluorophenyl) methanol (Compound [I])

Under a nitrogen atmosphere, turnings of magnesium (16.8 g) were dispersed in THF (46 ml), and iodine (0.1 g) was added. Then, 4-bromofluorobenzene (2.1 g) was added dropwise. After confirmation of the start of the reaction, THF (242 ml) was flown in. 4-Bromofluorobenzene (113.9 g) was added dropwise at 31.8–48.9° C., and the mixture was stirred at 38–40° C. for 2 hr. The obtained mixture with a Grignard reagent was cooled and thereto was added dropwise 2,4-dimethylbenzaldehyde (81 g) at 5–29.9° C. After the dropwise addition, the reaction mixture was stirred at 21.3–28.3° C. for 1.5 hr. A saturated aqueous ammonium chloride solution was added to stop the reaction. The reaction mixture was partitioned and the obtained organic layer was washed with saturated brine. The solvent was evaporated from the organic layer under reduced pressure to give (2,4-dimethylphenyl)-(4'-fluorophenyl)methanol (139.2 g, 100%) as a colorless oil. The obtained colorless oil was measured for $^1$H-NMR and found to be the same as in Example 1.

EXAMPLE 4

Synthesis of 4-(4'-fluorobenzoyl)isophthalic acid (Compound [II])

To (2,4-dimethylphenyl)-(4'-fluorophenyl)methanol (121 g) were added t-butyl alcohol (723 ml) and water (1090 ml) and the mixture was heated to 50° C. Potassium permanganate (582 g) was added at 50–75° C. over 6 hr. The reaction mixture was stirred at 70–85° C. for 3 hr and most of t-butyl alcohol was evaporated under reduced pressure. The by-produced manganese dioxide was filtered off and the obtained filtrate was neutralized with 6N hydrochloric acid. The generated crystals were collected by filtration and dried to give nearly pure 4-(4'-fluorobenzoyl)isophthalic acid (114.2 g, 75%) as white crystals.
$^1$H-NMR(DMSO-d$_6$, 400 MHz) δ=7.31(2H,t,J=9 Hz), 7.55(1H,d,J=8 Hz), 7.70(2H,dd,J=9 Hz,J=5 Hz), 8.23(1H, dd,J=8 Hz,J=2 Hz), 8.51(1H,d,J=2 Hz), 13.52(2H,br) ppm

EXAMPLE 5

Synthesis of 4-(4'-fluorobenzoyl)isophthalic acid (Compound [II])

To (2,4-dimethylphenyl)-(4'-fluorophenyl)methanol (121 g) were added t-butyl alcohol (703 ml) and water (578 ml) and the mixture was heated to 70° C. Potassium permanganate (548 g) was added at 70–80° C. over 32 hr. The reaction mixture was stirred at 70–85° C. for 3 hr and most of t-butyl alcohol was evaporated under reduced pressure. The by-produced manganese dioxide was filtered off and the obtained filtrate was neutralized with 6N hydrochloric acid. The generated crystals were collected by filtration and dried to give nearly pure 4-(4'-fluorobenzoyl)isophthalic acid (108.1 g, 71.4%) as white crystals. The obtained white crystals were measured for $^1$H-NMR and found to be the same as in Example 4.

EXAMPLE 6

Synthesis of 4-(4'-fluorobenzoyl)isophthalic acid (Compound [II])

To (2,4-dimethylphenyl)-(4'-fluorophenyl)methanol (121 g) were added a 87% aqueous solution (847 ml) of t-butyl alcohol and water (580.8 ml) and the mixture was heated to 69.9° C. Potassium permanganate (582 g) was added at 70.0–80.2° C. over 31 hr 20 min. The reaction mixture was stirred at 70–85° C. for 3 hr and most of t-butyl alcohol was evaporated under reduced pressure. The by-produced manganese dioxide was filtered off and the obtained filtrate was neutralized with 6N hydrochloric acid. The generated crystals were collected by filtration and dried to give nearly pure 4-(4'-fluorobenzoyl)isophthalic acid (108.4 g, 71.5%) as white crystals. The obtained white crystals were measured for $^1$H-NMR and found to be the same as in Example 4.

EXAMPLE 7

Synthesis of 1,3-dimethyl-4-(4'-fluorobenzoyl)benzene (Compound [I'])

To a suspension of anhydrous aluminum chloride (19.5 g) dispersed in m-xylene (150 ml) was added dropwise 4-fluorobenzoyl chloride (21.1 g) under ice-cooling. The mixture was stirred at 0–10° C. for 3 hr and poured into 6N hydrochloric acid. The reaction mixture was partitioned and the obtained organic layer was washed successively with water, 10% aqueous sodium hydroxide solution and water. The solvent was evaporated to give a 96:4 mixture (30.2 g, 99%) of 1,3-dimethyl-4-(4'-fluorobenzoyl)benzene and 1,3-dimethyl-2-(4,-fluorobenzoyl)benzene as pale-yellow oil.
1,3-Dimethyl-4-(4'-fluorobenzoyl)benzene
$^1$H-NMR(CDCl$_3$, 400 MHz) δ=2.32(3H,s), 2.38(3H,s), 7.05(1H,d,J=8 Hz), 7.11(2H,dd,J=9 Hz,J=7 Hz), 7.21(1H,d, J=8 Hz), 7.82(2H,dd,J=9Hz,J=5 Hz) ppm

EXAMPLE 8

Synthesis of 1,3-dimethyl-4-(41-fluorobenzoyl)benzene (Compound [I'])

To a suspension of anhydrous aluminum chloride (16.2 g) dispersed in 1,2-dichlorobenzene (150 ml) was added fluorobenzene (13 g), and thereto was added dropwise 2,4-dimethylbenzoyl chloride (17.0 g) at 0–20° C. The mixture was stirred at 10–30° C. for 1 hr and heated to 80° C. The mixture was stirred for 1 hr, cooled again and poured into 6N hydrochloric acid. The reaction mixture was diluted with a great excess toluene and partitioned. The obtained organic layer was washed successively with 5% aqueous sodium hydroxide solution and water, and the solvent was evaporated under reduced pressure. The residue was purified by silica gel column chromatography using cyclohexane-ethyl acetate as eluent to give nearly pure 1,3-dimethyl-4-(4'-fluorobenzoyl)benzene (19.4 g, 85%) as pale-yellow oil. The spectrum data of this oil were the same as those confirmed in Example 7.

EXAMPLE 9

Synthesis of 4-(4'-fluorobenzoyl)isophthalic acid (Compound [II])

Potassium permanganate (45 g) was dispersed in 25 w % aqueous t-butyl alcohol solution (110 g) and heated to 65° C. Thereto was added dropwise a t-butyl alcohol (28 ml) solution of a 96:4 mixture, synthesized in Example 7, (10 g) of 1,3-dimethyl-4-(4'-fluorobenzoyl)benzene and 1,3-dimethyl-2-(4'-fluorobenzoyl)benzene. After the dropwise addition, the mixture was reacted at 80–85° C. for 3 hr and most of t-butyl alcohol was evaporated under reduced pressure. The by-produced manganese dioxide was filtered off. The obtained filtrate was neutralized with 6N hydrochloric acid and the generated crystals were collected by filtration and dried to give nearly pure 4-(4'-fluorobenzoyl)isophthalic acid (9.9 g, 78%) as white crystals. The spectrum data of the crystals were the same as those in Example 4.

EXAMPLE 10

Synthesis of 4-(4'-fluorobenzoyl)isophthalic acid (Compound [II])

Trimellitic anhydride (20 g) and fluorobenzene (18.5 g) were dispersed in 1,2-dichlorobenzene (200 ml) and thereto was added anhydrous aluminum chloride (42 g). The mixture was stirred at 70–90° C. for 4 hr. The reaction mixture was poured into 4N hydrochloric acid (400 ml) and extracted with methyl isobutyl ketone (400 ml). The organic layer was extracted with 5% aqueous sodium hydroxide solution (240 g) and the aqueous layer was neutralized with 6N hydrochloric acid (64 g). The resulting crystals were collected by filtration, washed with water and dried to give a 7:3 mixture (22.4 g, 75%) of 4-(4'-fluorobenzoyl)-isophthalic acid and 2-(4'-fluorobenzoyl)terephthalic acid as white crystals.

The obtained mixture was recrystallized from methanol-water (8:5) to give nearly pure 4-(4'-fluorobenzoyl)isophthalic acid (6.8 g). The spectrum data of the crystals were the same as those in Example 4.

EXAMPLE 11

Synthesis of 4-(4'-fluorobenzoyl)isophthalic acid (Compound [II])

Trimellitic anhydride (20 g) and fluorobenzene (20 g) were dispersed in 1,2,4-trichlorobenzene (150 ml) and anhydrous aluminum chloride (42 g) was added. The mixture was stirred at 70–90° C. for 8 hr. The reaction mixture was poured into 4N hydrochloric acid (300 ml) in an ice bath, and the mixture was stirred at 50° C. for 3 hr and cooled. The resulting crystals were thoroughly washed with water, collected by filtration and dried to give a 65:35 mixture (19.1 g, 64%) of 4-(4'-fluorobenzoyl)-isophthalic acid and 2-(4'-fluorobenzoyl)terephthalic acid as white crystals.

4-(4'-Fluorobenzoyl)isophthalic acid $^1$H-NMR(DMSO-$d_6$, 400 MHz) δ=7.31(2H,t,J=9 Hz), 7.55(1H,d,J=8 Hz), 7.70(2H,dd,J=9 Hz,J=5 Hz), 8.23(1H,dd,J=8 Hz,J=2 Hz), 8.51(1H,d,J=2 Hz), 13.52(2H,br) ppm 2-(4'-Fluorobenzoyl)terephthalic acid $^1$H-NMR(DMSO-$d_6$, 400 MHz) δ=7.32(2H,t,J=9 Hz), 7.71(2H,dd,J=9 Hz,J=5 Hz), 7.87(1H,d,J=2 Hz), 8.09(1H,d,J=8 Hz), 8.17(1H,dd,J=8 Hz,J=2 Hz), 13.52(2H,br) ppm

COMPARATIVE EXAMPLE 1

Synthesis of 4-(4'-fluorobenzoyl)isophthalic acid (Compound [II])

Trimellitic anhydride (20 g) and fluorobenzene (20 g) were dispersed in nitrobenzene (200 ml) and anhydrous aluminum chloride (45 g) was added. The mixture was stirred at 70–90° C. for 6 hr. The reaction mixture was analyzed by HPLC, and as a result, 4-(4'-fluorobenzoyl)isophthalic acid was found to have been generated by 4%. The mixture was further stirred at 110–120° C. for 6 hr, but only the by-product (other than isomer) increased and the production rate of 4-(4'-fluorobenzoyl)isophthalic acid showed a propensity toward decrease.

EXAMPLE 12

Synthesis of 1-(4'-fluorophenyl)-1,3-dihydroisobenzofuran-5-ylmethanol (Compound [III])

To a suspension of sodium borohydride (2.5 g) dispersed in diethylene glycol dimethyl ether (40 ml) was added dropwise a solution of a 7:3 mixture, obtained in Example 10, (5.8 g) of 4-(4'-fluorobenzoyl)isophthalic acid and 2-(4'-fluorobenzoyl)-terephthalic acid in diethylene glycol dimethyl ether (29 ml) at 20–25° C., and the mixture was stirred for 10 min. Thereto was added dropwise boron trifluoride-THF complex (10.9 g) at 20–45° C., and the mixture was heated at 40–50° C. for 2 hr. After hydrolysis with water (50 ml) in an ice bath, 85% phosphoric acid (50 ml) was added, and the mixture was stirred at 60° C. for 5 hr. Water (200 ml) was added and the mixture was cooled. The generated crystals were collected by filtration, washed with water and dried to give crude 1-(4'-fluorophenyl)-1,3-dihydroisobenzofuran-5-ylmethanol (3.23 g). This was recrystallized twice from toluene to give nearly pure 1-(4'-fluorophenyl)-1,3-dihydroisobenzofuran-5-ylmethanol (2.10 g, 43%).

melting point 101–104° C. IR(KBr)ν=3214(br), 2848(w), 1606(s), 1511(s), 1225(s), 1157(m), 1135(m), 1046(s), 1015(s), 824(s), 810(s), 783(m)cm$^{-1}$ $^1$H-NMR(CDCl$_3$, 400 MHz)δ=4.72(2H,s), 5.19(1H,d,J=12 Hz), 5.31(1H,d,J=12 Hz), 6.14(1H,s), 6.98(1H,d,J=8 Hz), 7.03(2H,t,J=9 Hz), 7.24(1H,d,J=8 Hz), 7.29(2H,dd,J=9 Hz,J=6 Hz), 7.32(1H,s) ppm

EXAMPLE 13

Synthesis of 1-(4'-fluorophenyl)-1,3-dihydroisobenzofuran-5-ylmethanol (Compound [III])

To a suspension of sodium borohydride (14.6 g) dispersed in THF (120 ml) was added dropwise at 20–30° C. a solution of a 7:3 mixture (24.0 g), obtained in the same manner as in Example 10, of 4-(4'-fluorobenzoyl)isophthalic acid and 2-(4'-fluorobenzoyl)terephthalic acid in THF (240 ml). The mixture was heated to 55° C. and thereto was added dropwise dimethyl sulfate (47.0 g) at 55–65° C. After the dropwise addition, the mixture was refluxed for 5 hr, and hydrolyzed with water (72 ml) in an ice bath. THF was evaporated under reduced pressure. To the residue was added 85% phosphoric acid (48 g) and the mixture was stirred at 60° C. for 5 hr. Water (72 ml) was added and the mixture was cooled. The generated crystals were collected by filtration, washed with water and dried to give crude 1-(4'-fluorophenyl)-1,3-dihydroisobenzofuran-5-ylmethanol (15.1 g). This was recrystallized twice from toluene to give nearly pure 1-(4'-fluorophenyl)-1,3-dihydroisobenzofuran-5-ylmethanol (8.2 g, 40%). The various spectrum data of the crystals were the same as those obtained in Example 12.

EXAMPLE 14

Synthesis of 1-(4'-fluorophenyl)-1,3-dihydroisobenzofuran-5-ylmethanol (Compound [III])

To a suspension of sodium borohydride (15.0 g) dispersed in THF (130 ml) was added dropwise at 20–30° C. a solution of 4-(4'-fluorobenzoyl)isophthalic acid (26.0 g) synthesized in Example 4 in THF (260 ml) and the mixture was heated to 55° C. Dimethyl sulfate (51.0 g) was added dropwise at 55–65° C. After the dropwise addition, the mixture was refluxed for 5 hr, and hydrolyzed with water (130 ml) in an ice bath. THF was evaporated under reduced pressure. To the residue was added 85% phosphoric acid (52 g) and the mixture was stirred at 60° C. for 5 hr. Water (390 ml) was added and the mixture was cooled. The generated crystals were collected by filtration, washed with water and dried to give crude 1-(4'-fluorophenyl)-1,3-dihydroisobenzofuran-5-ylmethanol (20.4 g). This was recrystallized from a mixed solvent of ethyl acetate and heptane (2:3) to give nearly pure 1-(4'-fluorophenyl)-1,3-dihydroisobenzofuran-5-ylmethanol (18.9 g, 86%). The various spectrum data of the crystals were the same as those obtained in Example 12.

EXAMPLE 15

Synthesis of 1-(4'-fluorophenyl)-1,3-dihydroisobenzofuran-5-ylmethanol (Compound [III])

To a suspension of sodium borohydride (43.5 g) dispersed in THF (327 ml) was added trimethyl borate (9.1 g) and added dropwise at 20–30° C. a solution of 4-(4'-fluorobenzoyl)isophthalic acid (100.5 g) synthesized in Example 4 in THF (313 ml), and the mixture was heated to 35° C. A boron trifluoride-THF complex (181.7 g) was added dropwise at 35–42° C. After the dropwise addition, the mixture was heated at 40–50° C. for 7 hr, and hydrolyzed with water (101 ml) in an ice bath. THF was evaporated under reduced pressure. To the residue was added 30% sulfuric acid (110 g) and the mixture was stirred at 60° C. for 5 hr. A 25% aqueous solution of sodium hydroxide (200 g) was added and the mixture was extracted with hot toluene (450 ml) at 70° C. The hot toluene layer was washed with warm water (70° C., 60 ml), heptane (450 ml) was added and the mixture was cooled. The precipitated crystals were collected by filtration and dried to give 1-(4'-fluorophenyl)-1,3-dihydroisobenzofuran-5-ylmethanol (69.0 g, 81%). The various spectrum data of the crystals were the same as those obtained in Example 12.

EXAMPLE 16

Synthesis of 1-(41-fluorophenyl)-1,3-dihydroisobenzofuran-5-ylmethanol (Compound [III])

To a suspension of lithium aluminum hydride (1.0 g) dispersed in THF (10 ml) was added dropwise at room temperature a solution of 4-(4'-fluorobenzoyl)isophthalic acid (3.0 g) in THF (30 ml), and the mixture was stirred for 10 hr. To the reduced reaction mixture was added 10% hydrochloric acid (10 ml) and the mixture was passed through celite. THF was evaporated under reduced pressure, and 85% phosphoric acid (10 g) was added. The mixture was stirred at 60° C. for 5 hr. To the reaction mixture was added water (50 ml) and the resulting crystals were collected by filtration and dried. The objective compound was separated by silica gel column chromatography to give 1-(4'-fluorophenyl)-1,3-dihydroisobenzofuran-5-ylmethanol (0.21 g, 8%). The various spectrum data of the crystals were the same as those obtained in Example 12.

EXAMPLE 17

Synthesis of 1-(41-fluorophenyl)-1,3-dihydroisobenzofuran-5-ylmethanol ylmethanol (Compound [III])

Sodium borohydride (40.3 kg) was added to THF (280. under a nitrogen atmosphere. Trimethyl borate (8.4 kg) wa dropwise at 20–30° C. and a solution of 4-(4'-fluorobenzoy isophthalic acid (93.1 kg) produced in the same manner as Example 4 in THF (280.3 kg) was added dropwise at 20–30° boron trifluoride-THF complex (173.3 kg, boron trifluoride was added dropwise at 35–42° C. and the mixture was reacted –42° C. for 3 hr and then at 48–50° C. for 4 hr. The reaction mixture was cooled to 0–5° C. and water (93.6 kg) was added dropwise at 0–25° C. The mixture was heated to 50–55° C. water (372 kg, 40–50° C.) was flown in. The mixture was he 50–85° C. and the solvent (637 kg) was evaporated at normal pressure. The reaction mixture was cooled to about 57° C. an sulfuric acid (102 kg) was flown in at 55–60° C. The reac mixture was stirred at 60–65° C. for 3 hr 50 min. By confi by HPLC, the triol compound (compound [VII]) was contained A 25% aqueous solution (186.6 kg) of sodium hydroxide was a dropwise at 20–40° C. and toluene (363 kg) was added. The n was heated at 75–80° C., extracted and stood for separation organic layer was washed with warm water (280 kg, 70–80° C. stood for separation. Warm water (55.6 kg, 70–80° C.) was a to the organic layer and the mixture was cooled to 25–30° C. Heptane (284 kg) was flown in at 25–30° C. and the mixture w aged for 1 hr, heated once to 40–42° C., cooled to 0–5° C. o hr and aged for 1 hr. The crystals were collected by filtra and washed with a mixture cooled to 0–5° C. containing tolue (40.7 kg) and heptane (31.5 kg). The crystals were dried un reduced pressure at about 45° C. for 15 hr and at 60–70° C. for to give 1-(4'-fluorophenyl)-1,3-dihydroisobenzofuran-5-ylmet (64.5 kg, yield 81.8%). Various spectrum data of the crysta were the same as those obtained in Example 12.

EXAMPLE 18

Synthesis of 1-(4'-fluorophenyl)-1,3-dihydroisobenzofuran-5-carbaldehyde (Compound [V])

1-(4'-Fluorophenyl)-1,3-dihydroisobenzofuran-5-ylmetha (299.3 g) and manganese dioxide (2.25 kg, type HMH, manufact by Toso) were dispersed in t-butyl methyl ether (3.4 L) and mixture was stirred at 10–30° C. for 6 hr. The reaction mixture was filtered and washed with t-butyl methyl ether (0.9 L). The solvent was evaporated under reduced pressure to give nearly pure 1-(4'-fluorophenyl)-1,3-dihydroisobenzofuran-5-carbaldehyde (258.2 g, 87%) as pale-yellow white crystals.

$^1$H-NMR(CDCl$_3$, 400 MHz)δ=5.25(1H,d,J=13 Hz), 5.38 (1H,d,J=13 Hz), 6.18(1H,s), 7.06(2H,t,J=9 Hz), 7.16(1H,d, J=8 Hz), 7.30(2H,dd,J=9 Hz,J=5 Hz), 7.77(1H,d,J=8 Hz), 7.83(1H,s), 10.03(1H,s) ppm

EXAMPLE 19

Synthesis of 1-(4'-fluorophenyl)-1,3-dihydroisobenzofuran-5-carbaldehyde (Compound [V])

1-(4'-Fluorophenyl)-1,3-dihydroisobenzofuran-5-yl-methanol (66.0 g) was dispersed in toluene (660 ml) and manganese dioxide (594 g, type HMH, manufactured by Toso) was added over 1 hr at 15–30° C. The mixture was stirred at 20–30° C. for 1 hr. The reaction mixture was filtered and washed with toluene (330 ml). The solvent was evaporated under reduced pressure to give nearly pure 1-(4'-fluorophenyl)-1,3-dihydroisobenzofuran-5-carbaldehyde (57.6 g, 88%) as pale-yellow white crystals. Various spectrum data of the crystals were the same as those obtained in Example 18.

EXAMPLE 20

Synthesis of 1-(4'-fluorophenyl)-1,3-dihydroisobenzofuran-5-carbaldehyde (Compound [V])

1-(4'-Fluorophenyl)-1,3-dihydroisobenzofuran-5-yl-methanol (60.5 kg) produced in Example 17 was added to toluene (520.9 kg) and manganese dioxide (544.8 kg, type HMH, manufactured by Toso) divided in three portions was added at 10–30° C. over 3 hr. The mixture was stirred at 23–27° C. for 1 hr, and the starting material was confirmed by HPLC to be 0.03%. Thereto were added Hyflo Super-Cel® (18.2 kg, Celite Co.) and anhydrous magnesium sulfate (30.2 kg). The mixture was cooled to about 100° C. over 2 hr and stirred at 2–10° C. for 40 min. The mixture was filtrated and the residue (waste manganese) was washed with toluene (284 kg). As a result of the analysis, 1-(4'-fluorophenyl)-1,3-dihydroisobenzofuran-5-carbaldehyde (60 kg, yield about 100%) was contained in the solution (917 kg). The crystals obtained by partial concentration of the solution showed the same physical properties as in Example 18.

EXAMPLE 21

Synthesis of 1-(4'-fluorophenyl)-1,3-dihydroisobenzofuran-5-carbonitrile (Compound [VI])

1-(4'-Fluorophenyl)-1,3-dihydroisobenzofuran-5-yl-methanol (50.0 g) and manganese dioxide (200 g, type HMH, manufactured by Toso) were dispersed in xylene (400 ml) and the mixture was stirred at 25–45° C. for 6 hr. The reaction mixture was filtered, and hydroxylamine hydrochloride (14.1 g) and triethylamine (20.5 g) were added. The mixture was stirred at 70–75° C. for 1 hr and acetic anhydride (75.3 g) was added. The mixture was stirred at 130–140° C. for 6 hr and water (180 ml) was added to the reaction mixture. Thereto was added 10% aqueous sodium hydroxide solution (100 g) and the mixture was partitioned. The solvent was evaporated under reduced pressure, and xylene (44 ml) and heptane (71 ml) were added at 60° C. The mixture was cooled to room temperature and the resulting crystals were collected by filtration and dried to give 1-(41-fluorophenyl)-1,3-dihydroisobenzofuran-5-carbonitrile (35.8 g, 73%) as pale-yellow crystals.

melting point 96–98° C. IR(KBr)ν=3050(w), 2867(m), 2228(s), 1603(s), 1510(s), 1224(s), 1157(m), 1048(s), 1031(s), 832(s)cm$^{-1}$ $^1$H-NMR(CDCl$_3$, 400 MHz)δ=5.21 (1H,d,J=13 Hz), 5.34(1H,d,J=13 Hz), 6.16(1H,s), 7.06(2H, t,J=9 Hz), 7.10(1H,d,J=8 Hz), 7.27(2H,dd,J=9 Hz,J=5 Hz), 7.55(1H,d,J=8 Hz), 7.60(1H,s) ppm

EXAMPLE 22

Synthesis of citalopram(1-(3-(dimethylamino)propyl)-1-(4'-fluorophenyl)-1,3-dihydroisobenzofuran-5-carbonitrile)

60% Sodium hydride (0.96 g) was dispersed in THF (20 ml), and to this suspension was added dropwise a solution of 1-(4'-fluorophenyl)-1,3-dihydroisobenzofuran-5-carbonitrile (5.0 g) in THF (10 ml) at 40–50° C. under a nitrogen atmosphere. Thereto was added tetra n-butylammonium bromide (0.2 g), and a solution of 3-(dimethylamino)propyl chloride (3.4 g) in t-butyl methyl ether (18 ml) was added dropwise, which was followed by stirring for 10 min. Further, 1,3-dimethyl-2-imidazolidinone (26.1 g, 25 ml) was added and the mixture was stirred at 61–64° C. for 6 hr. The reaction mixture was poured into ice water (83 ml) and extracted 3 times with toluene (33 ml). The organic layer was extracted 3 times with 20% aqueous acetic acid (41 ml), and the obtained aqueous layer was neutralized with 25% aqueous sodium hydroxide solution (120 g) and extracted 3 times with toluene (40 ml). The obtained organic layer was washed with water, and the solvent was evaporated to give 1-(3-(dimethylamino)propyl)-1-(4'-fluorophenyl)-1,3-dihydroisobenzofuran-5-carbonitrile (citalopram base) as a viscous oil (5.36 g, yield 79.1%).

$^1$H-NMR(CDCl$_3$, 400 MHz)δ=1.26–1.52(2H,m), 2.11–2.26(4H,m), 2.13(6H,s), 5.15(1H,d,J=13 Hz), 5.19 (1H,d,J=13 Hz), 7.00(2H,t,J=9 Hz), 7.39(1H,d,J=8 Hz), 7.43(2H,dd,J=9 Hz,J=5 Hz), 7.50(1H,s), 7.59(1H,d,J=8 Hz) ppm This oil was converted to hydrobromide by a conventional method and the obtained crystals had a melting point of 184–186° C. HPLC retention time and measurement conditions Retention time; 10.5 min
Column; manufactured by GL Sciences, Inertsil(trademark) ODS-2 4.6 mm×150 mm
Buffer solution; 0.01% aqueous trifluoroacetic acid solution
Mobile phase;acetonitrile:buffer solution=2:8–7:3, linear gradient is applied over 40 min
Flow rate; 1 ml/min

EXAMPLE 23

Synthesis of Citalopram

By the same reaction and post-treatment as in Example 22 except that N,N,N',N'-tetramethylethylenediamine (4.86 g) and N,N-dimethyl formamide (25 ml) were successively added instead of 1,3-dimethyl-2-imidazolidinone (26.1 g, 25 ml), 1-(3-(dimethylamino)-propyl)-1-(4'-fluorophenyl)-1,3-dihydroisobenzofuran-5-carbonitrile (citalopram base) was obtained as a viscous oil (5.13 g, yield 75.7%). Hydrobromide thereof showed the same HPLC retention time and melting point as obtained in Example 22.

EXAMPLE 24

Synthesis of Citalopram

60% Sodium hydride (0.58 g) was dispersed in THF (12 ml), and to this suspension was added dropwise a solution of 1-(4'-fluorophenyl)-1,3-dihydroisobenzofuran-5-carbonitrile (3.0 g) in THF (6 ml) at 40–50° C. under a nitrogen atmosphere. Thereto was added tetra n-butylammonium bromide (0.12 g), and a solution of 3-(dimethylamino)propyl chloride (2.0 g) in t-butyl methyl ether (12 ml) was added dropwise, which was followed by stirring for 10 min. Further, N,N,N',N'-tetramethylethylenediamine (0.73 g) and N,N-dimethylformamide (14.2 g, 15 ml) were added and the mixture was stirred at 61–64° C. for 7 hr. The reaction mixture was treated in the same manner as in Example 22 to give 1-(3-(dimethylamino)propyl)-1-(4'-fluorophenyl)-1,3-dihydroisobenzofuran-5-carbonitrile (citalopram base) as a viscous oil (3.14 g, yield 77.2%). Hydrobromide thereof showed the same HPLC retention time and melting point as obtained in Example 22.

EXAMPLE 25

Synthesis of Citalopram

By the same reaction and post-treatment as in Example 24 except that 1,3-dimethyl-2-imidazolidinone (6.3 g, 6 ml) and N,N-dimethylformamide (8.5 g, 9 ml) were added instead of N,N,N',N'-tetramethylethylenediamine (0.73 g) and N,N-dimethylformamide (15 ml), 1-(3-(dimethylamino)propyl)-1-(4'-fluorophenyl)-1,3-dihydroisobenzofuran-5-carbonitrile (citalopram base) was obtained as a viscous oil (2.88 g, yield 70.7%). Hydrobromide thereof showed the same HPLC retention time and melting point as obtained in Example 22.

COMPARATIVE EXAMPLE 2

Synthesis of Citalopram

In the same manner as in Example 22 except that the mixture was stirred as it was at 61–64° C. for 6 hr without adding 1,3-dimethyl-2-imidazolidinone (26.1 g, 25 ml), the reaction was carried out. As a result, the reaction hardly proceeded.

COMPARATIVE EXAMPLE 3

Synthesis of Citalopram

By the same reaction and post-treatment as in Example 22 except that N,N-dimethylformamide (23.6 g, 25 ml) was added instead of 1,3-dimethyl-2-imidazolidinone (26.1 g, 25 ml) and the mixture was stirred at 61–64° C. for 7 hr, 1-(3-(dimethylamino)-propyl)-1-(4'-fluorophenyl)-1,3-dihydroisobenzofuran-5-carbonitrile (citalopram base) was obtained as a viscous oil (4.12 g, yield 60.8%).

EXAMPLE 26

Synthesis of Citalopram

60% Sodium hydride (0.58 g) was dispersed in toluene (12 ml), and to this suspension was added dropwise a solution of 1-(4'-fluorophenyl)-1,3-dihydroisobenzofuran-5-carbonitrile (3.0 g) in THF (6 ml) at 40–50° C. under a nitrogen atmosphere. Thereto was added tetra n-butylammonium bromide (0.12 g), and a solution of 3-(dimethylamino)propyl chloride (2.0 g) in toluene (12 ml) was added dropwise, which was followed by stirring for 10 min. Further, N,N,N',N'-tetramethylethylenediamine (2.92 g) and dimethyl sulfoxide (15 ml) were added and the mixture was stirred at 61–64° C. for 7 hr. The reaction mixture was treated in the same manner as in Example 22 to give 1-(3-(dimethylamino)propyl)-1-(4'-fluorophenyl)-1,3-dihydroisobenzofuran-5-carbonitrile (citalopram base) as a viscous oil (2.79 g, yield 68.6%). Hydrobromide thereof showed the same HPLC retention time and melting point as obtained in Example 22.

EXAMPLE 27

Synthesis of Citalopram

Under nitrogen atmosphere, to a solution of 1-(4'-fluorophenyl)-1,3-dihydroisobenzofuran-5-carbonitrile (3.0 g) in N,N-dimethylformamide (15 ml) were added tetra n-butylammonium bromide (0.12 g) and N,N,N',N'-tetramethylethylenediamine (2.92 g). Thereto was added dropwise a solution of 3-(dimethylamino)propyl chloride (2.0 g) in toluene (12 ml), and then a suspension of 60% sodium hydride (0.58 g) and liquid paraffin (1.5 ml) over 1.5 hr. The mixture was stirred at 61–64° C. for 7 hr. The reaction mixture was treated in the same manner as in Example 22 to give 1-(3-(dimethylamino)propyl)-1-(4'-fluorophenyl)-1,3-dihydroisobenzofuran-5-carbonitrile (citalopram base) as a viscous oil (2.69 g, yield 66.1%). Hydrobromide thereof showed the same HPLC retention time and melting point as obtained in Example 22.

EXAMPLE 28

Synthesis of Citalopram

By the same reaction and post-treatment as in Example 27 except that dimethyl sulfoxide (15 ml) was used instead of N,N-dimethylformamide (15 ml), 1-(3-(dimethylamino)propyl)-1-(4'-fluorophenyl)-1,3-dihydroisobenzofuran-5-carbonitrile (citalopram base) was obtained as a viscous oil (2.68 g, yield 65.9%). Hydrobromide thereof showed the same HPLC retention time and melting point as obtained in Example 22.

EXAMPLE 29

Synthesis of Citalopram

Under a nitrogen atmosphere, to a solution of 1-(4'-fluorophenyl)-1,3-dihydroisobenzofuran-5-carbonitrile (9.00 g) in 1,3-dimethyl-2-imidazolidinone (54 ml) was added 60% sodium hydride (1.73 g) at room temperature. 3-(dimethylamino)propyl chloride hydrochloride (8.02 g) was neutralized with 10% aqueous sodium hydroxide solution (39 g) and extracted twice with toluene (13.5 ml). A toluene solution of 3-(dimethylamino)propyl chloride (about 6.1 g) obtained by dehydrating the extract with potassium carbonate and molecular sieves 3A was added dropwise to the above-mentioned red brown 1,3-dimethyl-2-imidazolidinone solution at room temperature under a nitrogen atmosphere. Tetra n-butylammonium bromide (0.36 g) and N,N,N',N'-tetramethylethylenediamine (4.37 g) were added and the mixture was stirred at 60–62° C. for 5 hr. The reaction mixture was poured into ice water (149 ml) and extracted 3 times with toluene (54 ml). The organic layer was extracted 3 times with 20% aqueous acetic acid solution (71 ml). The obtained aqueous layer was neutralized with 25% aqueous sodium hydroxide solution (210 g) and extracted 3 times with toluene (54 ml). The obtained organic layer was washed with water, and potassium carbonate (3.6 g) and silica gel (1.8 g) were added. The mixture was thoroughly stirred and filtered. The solvent was evaporated under reduced pressure to give 1-(3-(dimethylamino)propyl)-1-(4'-fluorophenyl)-1,3-dihydroisobenzofuran-5-carbonitrile (citalopram base) as a viscous oil (10.50 g, yield 86.0%). Hydrobromide thereof showed the same HPLC retention time and melting point as obtained in Example 22.

EXAMPLE 30

Synthesis of Citalopram

Sodium hydroxide (19.6 kg) was added to water (134 kg) for dissolution, and a 65.6% aqueous solution (60.7 kg) of 3-(dimethylamino)propyl chloride hydrochloride was added dropwise at 20–25° C. Toluene (58.2 kg) was added and the mixture was stirred and left standing to allow separation. Toluene (58.2 kg) was added to the aqueous layer and the mixture was stirred, which was followed by standing to allow separation. The organic layers were combined and powdery anhydrous potassium carbonate (9 kg) and molecular sieves 4A (1.7 kg) were added, which was followed by stirring for 1 hr. The mixture was filtrated and the residue was washed with toluene (27 kg) to give a solution of 3-(dimethylamino)propyl chloride in toluene.

A solution (639.9 kg, corresponding to 1-(4'-fluorophenyl)-1,3-dihydroisobenzofuran-5-carbonitrile, 44.8 kg) of 1-(4'-fluorophenyl)-1,3-dihydroisobenzofuran-5-carbonitrile in toluene obtained in the same manner as in Example 21 was concentrated under reduced pressure at 30–50° C. and toluene (539 kg) was evaporated. To the residue was added toluene (27 kg) and a solution of 3-(dimethylamino) propyl chloride prepared in advance in toluene was flown in, which was followed by the addition of 1,3-dimethyl-2-imidazolidinone (10 kg). Sodium hydride (64.8%, 9.1 kg) was added at 25–30° C. and 1,3-dimethyl-2-imidazolidinone (183 kg) was added dropwise at 25–60° C. over 4 hr 20 min. The mixture was reacted at 60–63° C. for 6 hr and cooled to about 10° C. The reaction mixture was analyzed by HPLC. As a result, the residual rate of 1-(4,-fluorophenyl)-1,3-dihydroisobenzofuran-5-carbonitrile was 0.1%.

The reaction mixture was added dropwise to water (806 kg) at about 5° C., and toluene (233.5 kg) was added. After stirring and extraction, the mixture was left standing to allow separation. Toluene (233.5 kg) was added to the aqueous layer and the mixture was stirred and extracted, which was followed by separation. The extracted organic layers were combined and stirred and extracted with a 5% aqueous solution (179 kg) of hydrochloric acid, which was followed by separation. The organic layer was again extracted with a 5% aqueous solution (179 kg) of hydrochloric acid and partitioned. The aqueous layers extracted with hydrochloric acid were combined. To the combined aqueous layer was added toluene (234 kg), and a 25% aqueous solution (89.6 kg) of sodium hydroxide was added dropwise at 25–35° C. to give an alkaline solution. The solution was stirred and extracted, which was stood to allow separation. The aqueous layer was again extracted with toluene (156.3 kg) and the organic layers were combined. The organic layer was washed three times with water (268.7 kg). The organic layer was dehydrated with powdery anhydrous potassium carbonate (17.9 kg), silica gel (Merk 9385, 6.7 kg) was added, and the mixture was stirred for 1 hr. The mixture was filtrated and the residue was washed with toluene (39.1 kg). Toluene was evaporated under reduced pressure at 40–65° C. The amount of the evaporated toluene was 425 kg. Acetone (35.5 kg) was added to the residue for dissolution to give a solution of citalopram in acetone. In the liquid amount (114.3 kg), citalopram base was contained by 52.96 kg (yield 87.2%). The HPLC retention time of hydrobromide of the crystals obtained by partial evaporation of acetone was the same as those in Example 22.

REFERENCE EXAMPLE 1

Synthesis of 1-(3-(dimethylamino)propyl)-1-(4'-fluorophenyl)-1,3-dihydroisobenzofuran-5-carbonitrile hydrobromide A solution (94.1 kg including citalopram 51.8 kg) of citalopram in acetone produced in Example 30 was added to acetone (163.4 kg) and hydrogen bromide (13.2 kg) was blown in over 3 hr at 25–35° C. After aging for 3 hr, the mixture was cooled to about 5° C. and aged at 0–5° C. for three more hours. The crystals were collected by filtration and washed with acetone (40.9 kg) cooled to 0–5° C. The crystals were dried under reduced pressure at 30–50° C. to give citalopram hydrobromide (54.9 kg, yield 83.7%).

Melting point: 180–183° C. Tapped density: 0.29 kg/L by standing, 0.32 kg/L by processing

REFERENCE EXAMPLE 2

Synthesis of 1-(3-(dimethylamino)propyl)-1-(41-fluorophenyl)-1,3-dihydroisobenzofuran-5-carbonitrile (Citalopram Base)

To a suspension of 60% sodium hydride (4.2 g) dispersed in THF (135 ml) was added dropwise at 40–50° C. a solution of 1-(4'-fluorophenyl)-1,3-dihydroisobenzofuran-5-carbonitrile (21.6 g) in THF (40 ml). The mixture was stirred at the same temperature for 30 min and a solution of 3-dimethylaminopropyl chloride (14.4 g) in t-butyl methyl ether (60 ml) was added dropwise. The mixture was stirred for 10 min and dimethyl sulfoxide (135 ml) was added dropwise. The mixture was stirred at 60–70° C. for 5 hr. The reaction mixture was poured into ice water (800 ml) and extracted 3 times with toluene (250 ml). The organic layer was extracted twice with 20% aqueous acetic acid solution (250 ml). The aqueous layer was neutralized, extracted twice with toluene (250 ml) and washed with water. The solvent was evaporated to give 1-(3-(dimethylamino)propyl)-1-(4'-fluorophenyl)-1,3-dihydroisobenzofuran-5-carbonitrile (citalopram base) as a viscous oil (17.9 g, 61.1%).

$^1$H-NMR(CDCl$_3$, 400 MHz)δ=1.26–1.52(2H,m), 2.11–2.26(4H,m), 2.13(6H,s), 5.15(1H,d,J=13 Hz), 5.19 (1H,d,J=13 Hz), 7.00(2H,t,J=9 Hz), 7.39(1H,d,J=8 Hz), 7.43(2H,dd,J=9 Hz,J=5 Hz), 7.50(1H,s), 7.59(1H,d,J=8 Hz) ppm This oil was converted to hydrobromide by a conventional method and the obtained crystals had a melting point of 184–186° C.

As described in the foregoing, the production method of the present invention enables industrial and economical production of citalopram useful as an antidepressant, at a high yield. The new production method of compound [III], which is a key compound for the synthesis of citalopram, can widen the possibility of the synthesis of compound [III].

This application is based on patent application Nos. 039936/2000 and 065527/2000 filed in Japan, the contents of which are hereby incorporated by reference.

What is claimed is:

1. A method for the preparation of citalopram, which method comprises the steps of (a) reducing the compound of formula [II]

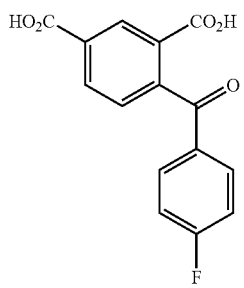

to form a compound of formula [VII]

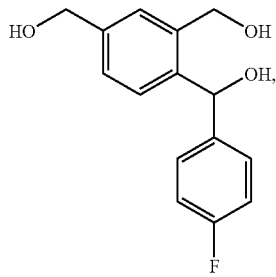

(b) cyclizing the compound of formula [VII] to form a compound of formula [III]

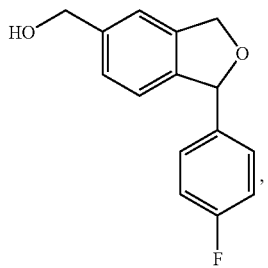

(c) oxidizing the compound of formula [III] to form an aldehyde compound of formula

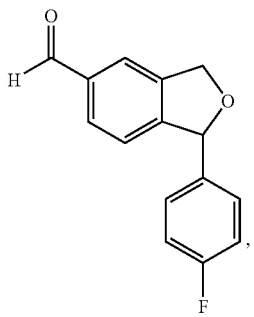

(d) converting the aldehyde compound of formula [V] to the corresponding 5-cyano compound of formula [VI]

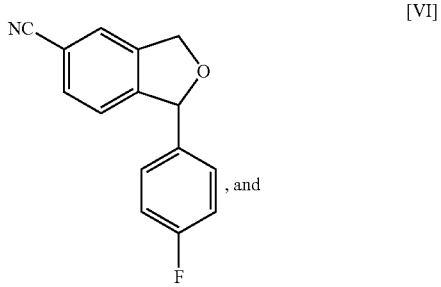

(e) alkylating the 5-cyano compound of formula [VI] to form citalopram in the form of a base or an acid addition salt thereof.

2. The method of claim 1, wherein the method further comprises the step of (f) isolating the citalopram in the form of a base or an acid addition salt thereof.

3. The method of claim 1, wherein the compound of formula [III] is oxidized to form the aldehyde compound of formula [V] by reacting the compound of formula [III] with manganese dioxide to form the aldehyde compound of formula [V].

4. The method of claim 3, wherein the method further comprises the step of (f) isolating the citalopram in the form of a base or an acid addition salt thereof.

5. The method of claim 3, wherein the aldehyde compound of formula [V] is convened to the corresponding 5-cyano compound of formula [VI] by the steps of (d1) condensing the aldehyde compound of formula [V] with hydroxylamine or a mineral acid salt thereof to form an oxime intermediate, and (d2) dehydrating the oxime intermediate to form the 5-cyano compound of formula [VI].

6. The method of claim 5, wherein the method further comprises the step of (f) isolating the citalopram in the form of a base or an acid addition salt thereof.

7. The method of claim 1, wherein the aldehyde compound of formula [V] is converted to the corresponding 5-cyano compound of formula [VI] by the steps of (d1) condensing the aldehyde compound of formula [V] with hydroxylamine or a mineral acid salt thereof to form an oxime intermediate, and (d2) dehydrating the oxime intermediate to form the 5-cyano compound of formula [VI].

8. The method of claim 7, wherein the method further comprises the step of (f) isolating the citalopram in the form of a base or an acid addition salt thereof.

* * * * *